United States Patent
Gründler et al.

(10) Patent No.: US 9,566,409 B2
(45) Date of Patent: Feb. 14, 2017

(54) DEVICE AND METHOD FOR TEMPERING AND HUMIDIFYING GAS, ESPECIALLY RESPIRATORY AIR

(71) Applicant: Gründler Gmbh, Freudenstadt (DE)

(72) Inventors: Christoph Gründler, Freudenstadt (DE); Markus Gründler, Freudenstadt (DE); Daniel Heine, Dornstetten (DE)

(73) Assignee: RESMED HUMIDIFICATION TECHNOLOGIES GMBH, Freudenstadt (DE)

( * ) Notice: Subject to any disclaimer, the term of this patent is extended or adjusted under 35 U.S.C. 154(b) by 1 day.

(21) Appl. No.: 14/025,595

(22) Filed: Sep. 12, 2013

(65) Prior Publication Data

US 2014/0007872 A1    Jan. 9, 2014

Related U.S. Application Data

(63) Continuation of application No. 13/171,793, filed on Jun. 29, 2011, now Pat. No. 8,544,461, which is a
(Continued)

(30) Foreign Application Priority Data

Oct. 31, 2002   (DE) .................. 102 51 134

(51) Int. Cl.
*A61M 16/16* (2006.01)
*A61M 16/10* (2006.01)
(Continued)

(52) U.S. Cl.
CPC ........... *A61M 16/16* (2013.01); *A61M 13/003* (2013.01); *A61M 16/10* (2013.01); *A61M 16/108* (2014.02);
(Continued)

(58) Field of Classification Search
CPC ...... A61M 16/16; A61M 16/14; A61M 16/10; A61M 16/162; A61M 16/164; A61M 16/165; A61M 16/167; A61M 16/168; A61M 16/1075; A61M 16/1045; A62B 18/088; A62B 9/003; A62B 9/006
(Continued)

(56) References Cited

U.S. PATENT DOCUMENTS 2,162,462 A   6/1939   Reid
3,987,133 A   10/1976  Andra
(Continued)

FOREIGN PATENT DOCUMENTS

DE   28 34 622   2/1979
DE   37 30 551   3/1989
(Continued)

OTHER PUBLICATIONS

International Search Report, PCT/EP2003/012140, Jul. 15, 2004.

*Primary Examiner* — Justine Yu
*Assistant Examiner* — Colin W Stuart
(74) *Attorney, Agent, or Firm* — Nixon & Vanderhye, P.C.

(57) ABSTRACT

A device and a process for the heating and humidification of gas, especially respiratory gas. Fluid from a fluid reservoir is supplied to a sprinkling type chamber where, for the purpose of humidification, it is moved through the gas. The point is that the fluid is heated by a temperature controlled heater to a preset temperature. In addition to the description of the device, a description of the process underlying the operation of the device is described.

20 Claims, 3 Drawing Sheets

Related U.S. Application Data continuation of application No. 10/531,058, filed as application No. PCT/EP03/12140 on Oct. 31, 2003, now Pat. No. 7,975,687.

(51) Int. Cl.
*A61M 13/00* (2006.01)
*F24F 6/02* (2006.01)
*A61M 16/20* (2006.01)

(52) U.S. Cl.
CPC ....... *A61M 16/109* (2014.02); *A61M 16/1075* (2013.01); *A61M 16/162* (2013.01); *F24F 6/025* (2013.01); *A61M 16/20* (2013.01); *A61M 2205/3389* (2013.01); *A61M 2205/7563* (2013.01)

(58) Field of Classification Search
USPC .......... 128/200.21, 200.11, 201.13, 204.17,128/205.18, 203.26, 200.24, 203.16, 203.17,128/204.14; 239/135
See application file for complete search history.

(56) References Cited

U.S. PATENT DOCUMENTS

| | | | |
|---|---|---|---|
| 4,010,748 A | 3/1977 | Dobritz | |
| 4,026,285 A | 5/1977 | Jackson | |
| 4,121,583 A | 10/1978 | Chen | |
| 4,541,966 A | 9/1985 | Smith | |
| 4,566,450 A | 1/1986 | Brossman | |
| 4,829,781 A | 5/1989 | Hitzler | |
| 5,172,686 A | 12/1992 | Anthony | |
| 5,497,628 A | 3/1996 | Stueble | |
| 5,524,848 A | 6/1996 | Ellsworth | |
| 5,855,823 A | 1/1999 | MacGibbon et al. | |
| 5,890,490 A * | 4/1999 | Aylsworth et al. | 128/203.12 |
| 6,010,118 A | 1/2000 | Milewicz | |
| 6,068,609 A | 5/2000 | Ott et al. | |
| 6,102,037 A | 8/2000 | Koch | |
| 7,314,046 B2 * | 1/2008 | Schroeder et al. | 128/200.14 |
| 7,975,687 B2 | 7/2011 | Grundler et al. | |
| 8,544,461 B2 * | 10/2013 | Grundler et al. | 128/200.11 |
| 2002/0100320 A1 * | 8/2002 | Smith et al. | 73/431 |
| 2002/0139367 A1 * | 10/2002 | McPhee | 128/203.17 |
| 2003/0066526 A1 | 4/2003 | Thudor | |
| 2005/0061318 A1 * | 3/2005 | Faram | A61M 16/127 128/204.18 |
| 2006/0151624 A1 | 7/2006 | Grundler et al. | |

FOREIGN PATENT DOCUMENTS

| | | |
|---|---|---|
| DE | 38 30 314 | 3/1989 |
| DE | 37 35 219 | 4/1989 |
| DE | 43 03 645 | 8/1994 |
| DE | 43 12 793 | 10/1994 |
| DE | 94 17 169 | 12/1994 |
| DE | 44 32 907 | 3/1995 |
| DE | 296 12 115 | 9/1996 |
| DE | 197 26 110 | 1/1999 |
| DE | 197 27 884 | 2/1999 |
| DE | 100 49 869 | 4/2002 |

* cited by examiner

DEVICE AND METHOD FOR TEMPERING AND HUMIDIFYING GAS, ESPECIALLY RESPIRATORY AIR

CROSS-REFERENCE TO RELATED APPLICATIONS

This application is a continuation of U.S. application Ser. No. 13/171,793, filed Jun. 29, 2011, now U.S. Pat. No. 8,544,461, which is a continuation of U.S. patent application Ser. No. 10/531,058, now U.S. Pat. No. 7,975,687, filed Jan. 17, 2006, which is a national phase entry of PCT/EP2003/012140, filed Oct. 31, 2003, which claims priority to German Application No. 102 51 134.9, filed Oct. 31, 2002, the entire contents of each of which are hereby incorporated by reference.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a device to heat and humidity gas, especially respiratory gas. The device comprises a fluid reservoir, a humidification chamber with gas inlet and outlet, and a device to move the fluid through the gas. Furthermore, the invention relates to such a process.

Such a device and process should be used especially for the artificial ventilation of a patient. With respect to the here presented invention, "ventilation" comprises each type of respiratory therapy, and "patient" comprises as well human as well as animal patients.

2. Description of Related Art Including Information Disclosed Under 37 CFR 1.97 and 37 CFR 1.98.

Traditionally such a type of patient ventilation is performed using a device with a respiratory tubing, a device to generate the gas flow directed to the patient ("gas flow generator"), and a respiratory gas humidifier. Traditionally the respiratory gas is taken from a reservoir and directed to the gas flow generator, and the gas flow generator is equipped with a gas outlet connecting to the respiratory tubing. The main feature of such a gas flow generator is that it is capable to control pressure and/or volume and/or flow of the respiratory gas directed to the patient for instance by means of valves or a bellow. The gas flow generator may be a separate device, or it may be integrated into another device.

Usually the respiratory gas is a mixture of air and oxygen, but other special gas mixtures may be used as well.

Usually, the fluid within the fluid reservoir which is used to humidify the respiratory gas (air; mixture of air and oxygen; else) is water. Within the scope of the here presented invention one could imagine to use water as well as other fluids, or a mixture of different fluids, with or without added drugs.

Most artificially ventilated patients are ventilated via an endotracheal tube. This tube connects to the distal end of a respiratory tubing leading the respiratory gas from the respiratory gas flow generator to the patient. The tube may well simultaneously connect to several other respiratory tubings.

Usually, the respiratory gas delivered by the respiratory gas flow generator is controlled by several parameters in order to adapt the respiratory gas flow to the patient's individual needs. The set parameters are automatically controlled by the respiratory gas flow generator or may be adjusted according to requirements. Depending on the model of respiratory gas flow generator used and its control settings the instantaneous respiratory gas flow may vary widely during a single respiratory cycle which when using so far known ventilators may lead to serious problems.

The endotracheal tube bypasses nose, pharynx and larynx thus eliminating their normal function of heating and humidification of the respiratory gas. While using a face mask for the application of continuous positive airway pressure (CPAP), nose and pharynx/larynx are functionally maintained. During respiratory therapy, however, the significantly higher and often continuous gas flow with reference to normal breathing—especially when using cold and dry respiratory gas—often leads to adverse effects, i.e. irritation, inflammation, dryness and incrustation of the upper airways.

In order to overcome those problems, during respiratory therapy the respiratory gas taken from a reservoir (i.e. pressurized gas from a bottle or wall outlet), or from the environment via fan or bellow etc., which usually is quite dry is artificially humidified and heated.

The aim is to emulate the natural conditions that is to heat the respiratory gas to body temperature and to humidity it to nearly full saturation. The aim is to reach a saturation of 95 to 100% relative humidity.

That task is quite difficult to perform especially under circumstances as described above where the instantaneous respiratory gas flow is widely varying as during spontaneous breathing or artificial ventilation.

Similar difficulties exist in other medical areas than respiratory therapy, i.e. laparoscopy, and there devices similar to the here presented invention may be used. During laparoscopy, for purposes of expansion a gas (frequently used gas: carbon dioxide) is insufflated into a body cavity (e.g. abdomen). In that application and similar ones, heating and humidification of the gas to nearly saturation is capable to prevent the quite frequent adverse effects of mucosal irritation and drying and cooling.

It is important to note that also in laparoscopy the gas flow shows remarkably high variations in time, since the insertion of instruments into or their removal from body openings requires a fast gas flow control in order to maintain a constant pressure within the body cavity.

Principally, there are several techniques and processes known to heat and humidify gas to preset values in the applications mentioned above. The following describes some of those processes and the corresponding devices.

Pass-Over Humidifier (e.g. DE 38 30 314)

This known device uses a reservoir filled with heated water. The respiratory gas is conducted along the water's surface thus heating and at the same time humidifying the gas. The water at the surface will cool down due to evaporation and is rather slowly replaced by warmer water mounting from beneath.

The area of the water/gas interface is limited due to the limited space available in the practical respiratory setting. In conjunction with the cooling of the surface water and its but slow replacement with warmer water (see above) resulting in a slow energy transfer to the water surface such a humidifier will deliver gas with a temperature highly dependent on gas flow, i.e. a varying gas-fluid temperature difference. This is why with that humidifier design the water's temperature is set according to the temporal average gas flow. In conventional devices this temperature is between about 40 and 80° C. Hence the instantaneous temperature and humidity of a heavily varying gas flow which is commonly seen in respiratory therapy (see above) is either too high or too low. A theoretical but technically impractical solution would be a very fast water temperature control.

Membrane-Type Humidifier (e.g. DE 43 03 645)

With such a device gas is directed over the surface of a structured body protruding from the heated fluid. The structured body is sucking from the reservoir the amount of fluid needed, e.g. by capillary forces. Only the amount of fluid just evaporated is replaced by fresh heated fluid. The most significant disadvantage of that design is that there arise similar problems as with the pass-over humidifier, since there is generated evaporation coldness which is not compensated for as fast as needed due to the rather slow energy transfer by the heated water rather slowly replacing the evaporated water, resulting in the inability to humidify or heat a highly variable gas flow impossible to constant values. The life-time of most of the structured bodies on the market is limited, and most of them are not fully autoclavable which is disadvantageous with respect to medical applications.

Fibre-Type Humidifier (e.g. DE 197 27 884)

Partially permeable hollow fibers (e.g. from PTFE) are bundled, and the gas to be heated and humidified is directed through their luminae. The outer surface of the fibers is in contact with the fluid needed for humidification. The disadvantage of that design is the fibers' limited life-time and mechanical as well as thermal durability. Moreover, the fibers' unsuitably high thermal resistance unduly restricts the heat transfer needed to compensate for evaporation coldness. Thus especially with high gas flow the heating of the gas is insufficient, which in turn leads to insufficient gas humidification. From theory increasing the water's temperature might compensate for those limitations. In case of a heavily varying gas flow, however, even forced heating of the fibers will not lead to constant humidification due to technical limitations of controlling the instantaneous fibre temperature as fast as required.

High-Temperature Humidifier (e.g. DE 43 12 793)

With such devices small quantities of fluid are evaporated at temperatures of about 80° C. to 130° C. and mixed with the gas flow, thus providing both the energy to heat the gas and the humidity as required. Main disadvantage of those devices is the high technical complexity needed which is paralleled by an increased technical risk especially with respect to high pressure and heat. Another disadvantage is that for technical reasons the control of the evaporation lags behind the demands. With heavily varying gas flow this will result in inconstant heating and humidification.

Bubble Through Humidifier (e.g. DE 37 30 551)

With those devices gas is bubbling through a heated fluid, resulting in heating and humidifying of the gas. The main disadvantage of that design is its high gas flow resistance which numerically is at least the pressure difference resulting from the fluid surface to the level where the gas is entering the fluid. Especially in spontaneously breathing patients a high gas flow resistance is disadvantageous.

Ultrasound-Type Nebulizer (e.g. DE 197 26 110)

Those devices use ultrasound to induce fluid vibrations resulting in the generation of tiny droplets which enter the gas flow. Main disadvantage of that design is that the "humidification" does not result in molecular fluid within the gas but in substantially larger fluid particles (generation of an aerosol). In contrast to molecular fluid, those larger particles have the potential to transport pathogens to the patient. There is also the risk that—especially with intermittent or varying gas flow—the amount of humidity is too high or too low.

Pressure-Type Nebulizer (e.g. DE 28 34 622)

Those devices nebulize a fluid resulting in the formation of tiny droplets, not molecular fluid. Thus those devices inherit the same disadvantages as ultrasound-type nebulizers (see above).

Heat and Moisture Exchanger ("HME" e.g. DE 94 17 169), Filter Pads, Etc.

With heat and moisture exchangers ("artificial noses") the gas is directed over a very large wet surface which results in saturation of the gas with humidity. The "artificial nose" extracts the heat and humidity needed from the patient's expiratory gas. Filter pads e.g. from air conditioning technique get the heat and humidity needed from a water bath or similar device. While heating and humidifying, the gas filter pads filtrate it from particles.

In all those devices, it is of disadvantage that the evaporation coldness results in a gas flow dependent decrease in gas temperature. Thus with varying gas flow it is impossible to provide constant gas temperature and humidity. The amount of particles adhering to the filter will increase with time resulting in an increase in gas flow resistance which is highly undesirable in the medical setting. Since by design HME have to be placed in the patient's inspiratory as well as expiratory gas stream they increase the dead space with the result that the patient will inspire more or less his expiratory gas.

Booster Systems (e.g. DE 44 32 907)

With those systems it is tried to compensate for the insufficient efficiency of an "artificial nose" (HME) by means of adding both fluid and heat which requires a technically demanding control circuitry. By design, a heavily varying gas flow will result in inconstant gas temperature and humidity, since even the best control circuit is incapable to compensate for the evaporation coldness without significant time lag. Of disadvantage are also the system's increased dead space (see above), its large dimension and weight, and other features not discussed here.

A Combination of the Above Mentioned Systems (e.g. DE 296 12 115)

With this combined design, first the gas is overheated and humidified. Then in a following second step, the gas is cooled down to target temperature by means of metal lamellas or equivalent. During that step, any humidity above saturation will form condensate dripping from the metal lamellas. The condensate is recirculated to the humidifier. With this process, it is of disadvantage that at first more energy in form of humidity and temperature is added to the gas than needed for ventilation.

This is not only unfavorable from an energetic point of view but there is also the risk that any malfunction of the cooling system will result in a substantial damage to the patient.

Ambient Air Humidifier with a Stack of Rotating Plates (e.g. DE 37 35 219)

Those systems inherit a stack of rotating plates which during a part of each rotation dip into water thus becoming wet. A fan drives the gas along those stacks. The idea is that so the gas will be both cleared from any particles, and humidified. Those systems need a non-volatile additive in the fluid to reduce the fluid's surface tension thus allowing for a sufficient wetting of the stack of plates. Such, or similar, devices are intended for use on climatization of living spaces. They lack any possibility to heat the gas to a preset value. The practically limited mechanical dimension of those systems as well as their rotation frequency render them unsuitable for constant humidification of a varying gas flow, or to saturate it with humidity.

Thus to summarize, the state-of-the-art gas heating and humidifying systems are unsuitable for a satisfying controlled heating and humidification of a heavily varying or intermittent gas flow. Under those conditions, the so far known systems produce a gas with heavily varying temperature and humidity.

Another disadvantage of the known systems is that they impair—some of them to a very high degree—the precision of measurements and regulatory control loops highly desirable in respiratory therapy, or they hinder them totally. For instance, in ventilatory support applications some methods and sensors require the direct coupling of the respiratory gas flow generator or a sensor to the patient in order to deliver the respiratory gas in a preset and constant quality and quantity, for instance a precise volume flow.

Disadvantages of the already known humidifier devices placed between the respiratory gas flow generator and the patient are that they add an extra compressible volume—sometimes of extraordinary magnitude—to the respiratory circuit.

Another disadvantage of some of the already known humidifier devices is the positive pressure gradient between gas inlet and outlet. Since the pressure of the respiratory gas given to the patient (level of respiration gas) is only marginally higher than the pressure of the ambient air (pressure difference usually max. 0.1 bar) the pressure within the gas flow generator is not the same as that directly at the patient. In consequence, there is the risk of malfunction and imprecise pressure control.

BRIEF SUMMARY OF THE INVENTION

Thus the object of the present invention is an improved system for gas heating and humidification in such a way that the named disadvantages of the already known systems are eliminated. A special object of the invented system is that it is capable to heat the gas independent from any gas flow variations to a preset temperature, and to humidify it at this temperature with a fluid to nearly saturation (i.e. relative humidity of about 95 to 100%).

In the invention of a device for the heating and humidification of a gas this task is performed by means of a temperature-controlled fluid heater as integral part of the system which in addition comprises a fluid reservoir, a humidification chamber, a gas inlet, a gas outlet, and a drive device used to force the fluid through the gas.

In many respects, the invention is advantageous over already known systems which represent the state-of-the-art:

Firstly, it provides two elements (namely the drive device and the temperature-controlled heater) which may be used to control for temperature and humidification.

Secondly, those two elements which may be controlled independently allow for a quite intense heating and humidification, which in turn makes it possible to reduce the physical dimension of the device to a handy one.

In addition, a device according to the invention may be constructed to withstand heavy duty, and to be dependable even with continuous use.

There is no aerosol formation. Instead, the gas is saturated with molecular fluid. It is of special significance that both temperature and humidity are easily controlled by means of the drive device and the temperature-controlled heating circuitry.

An effective design is to use a sprinkling type humidification chamber. In such a chamber, the fluid is moved through the gas. The temperature of the gas flow will easily approximate the fluid's temperature. At the same time, the gas flow will be saturated with evaporated fluid. The gas at the gas outlet of the chamber will be saturated (relative humidity between about 95 to 100%) with a temperature close to the fluid's temperature.

It will be advantageous if the sprinkling type humidification chamber is filled with a filing material providing a huge fluid/gas interface. During operation, the temperature of this filling material will become the same as that of the fluid due to its intimate contact to the fluid and the steady fluid turn-over. Physically spoken, this filling material is a temperature and energy buffer which immediately will provide some extra energy for evaporation if needed in case the gas flow is heavily varying.

Hence especially suited for this purpose are fillings of either knitted aluminum, stainless steel wool, or metal (especially stainless steel) pearls. Those materials inherit a large energy storage capacity combined with the feature to release energy quickly.

However, for the filling material one could also use other materials with open pored structure.

It is of importance to choose the filling material such that in fluidic aspects it will not significantly impair the gas flow thus preventing any significant pressure gradient between gas inlet and outlet even with maximal gas flow.

Preferably such a filling material should be easy to remove from the sprinkling type chamber for the purposes of change or sterilization.

In addition it is important that the drive device (preferably a pump) which moves the fluid through the gas has the capacity to circulate an amount of warmed fluid through the sprinkling type chamber (which may be filled with filling material) sufficient to provide the energy required to increase the gas temperature, and for fluid evaporation. Even with maximal gas flow, those means will guarantee that the flowing gas' temperature will approximate that of the fluid, and that the gas at the outlet will be nearly saturated with humidity.

In practice for certain applications, it was advantageous to increase the working pressure of the humidification chamber.

Doing so allows to feed the gas flow generator being situated downstream of the humidification chamber with already humidified gas thus avoiding the need to place the humidifier between the gas flow generator and the patient. Hence, there is neither a compressible volume nor a pressure gradient added between gas flow generator and patient which is highly desirable.

Moreover, pressurized humidification will humidify and store a substantially larger amount of gas than a low-pressure humidification placed in the low-pressure area between gas flow generator and patient. In consequence, pressurized humidification is an effective buffer of heated and humidified gas, which is of special importance when working with a fast fluctuating gas flow.

There is no need for a sophisticated control circuitry. This substantially simplifies the system, reflected in reduced costs.

In order to exactly set the temperature of the gas flowing out of the gas flow generator to the patient it is proposed to supply the respiratory tubing with an active heater which may be placed in the lumen of the respiratory tubing. Alternatively, the heater element may be integral part of the respiratory tubing's wall. Integrating the heater element into the respiratory tubing has the advantages that the heater element is in direct contact with the respiratory gas, and that it can be exactly heated to the target temperature thus making it easier to maintain a constant gas temperature at the patient site even with heavily varying gas flow.

One should also mention that while using a pressurized humidifier, the fluid, and in consequence the humidification process, is set to such a temperature that after depressurization of the humidified and heated gas to respiratory or environmental pressure/conditions, and at the selected target ventilatory temperature the gas humidity exactly meats the requirements. Preferably, in ventilatory applications the target gas humidity is near saturation.

Principally the temperature of the pressurized humidification chamber is dependent both on the pressure within the humidifier, and on the target temperature and relative humidity of the respiratory gas at the patient site. Depending on the type of application it might well be that the relative gas target humidity at the patient site is less than 100%.

The invention covers also the possibility to vary the pressure within the humidifier according to the variations of the respiratory gas flow in order to deliver after depressurization at the patient site a gas of constant temperature and humidity.

That part of the fluid which does not directly contribute to gas humidification but to gas heating will decrease its temperature at the sprinkling element. In the preferred embodiment, after reheating by the temperature-controlled heater, it will be recirculated to the fluid reservoir from which it may be recirculated to the sprinkling element.

In such a circulating system it is preferable to integrate a filter in order to guarantee for almost sterility of both the circulating fluid and the respiratory gas.

In another preferred embodiment the fluid reservoir where the temperature-controlled heater is placed is unpressurized and coupled via a pump (working as drive device for the fluid) to the sprinkling element. By controlling this pump it is possible to adapt the amount of circulated fluid per time unit to the actual needs. Switching a pressure regulator into the fluid circulation allows for uninterrupted operation of the heating and humidification device even when there is need to refill fluid into the fluid reservoir.

Of course the sprinkling type humidifier is suitable for low-pressure humidification, too, maintaining its advantages as mentioned above. Its integration into a ventilator circuit, however, might result in undesired additional compressible volume.

An alternative embodiment does not use a pump but a rotating body partially submerged into the fluid within the fluid reservoir to keep the fluid moving. Preferably this body consists of a stack of multiple plates set at distance to each other which while rotating around a horizontal axis delivering fluid from the fluid reservoir into the gas stream. There the fluid evaporates and humidifies the gas. Such a device may be constructed in a very compact design, and if electrically driven the rotation of the stack is very easy to control thus enabling the system to react quickly to varying fluid needs for humidification arising from a varying gas flow.

Another significant feature of the invention is that the control of the target parameters may be ensured by control of the fluid level within the fluid reservoir, and of both temperature and pressure within the humidification chamber in combination with the measurement of temperature and relative humidity of the respiratory gas at the patient site. Those tasks are technically easy to perform.

BRIEF DESCRIPTION OF THE SEVERAL VIEWS OF THE DRAWINGS

Further advantages and features of the invention are given by the following descriptions of the exemplary embodiment.

DETAILED DESCRIPTION OF THE INVENTION

Figure 1:
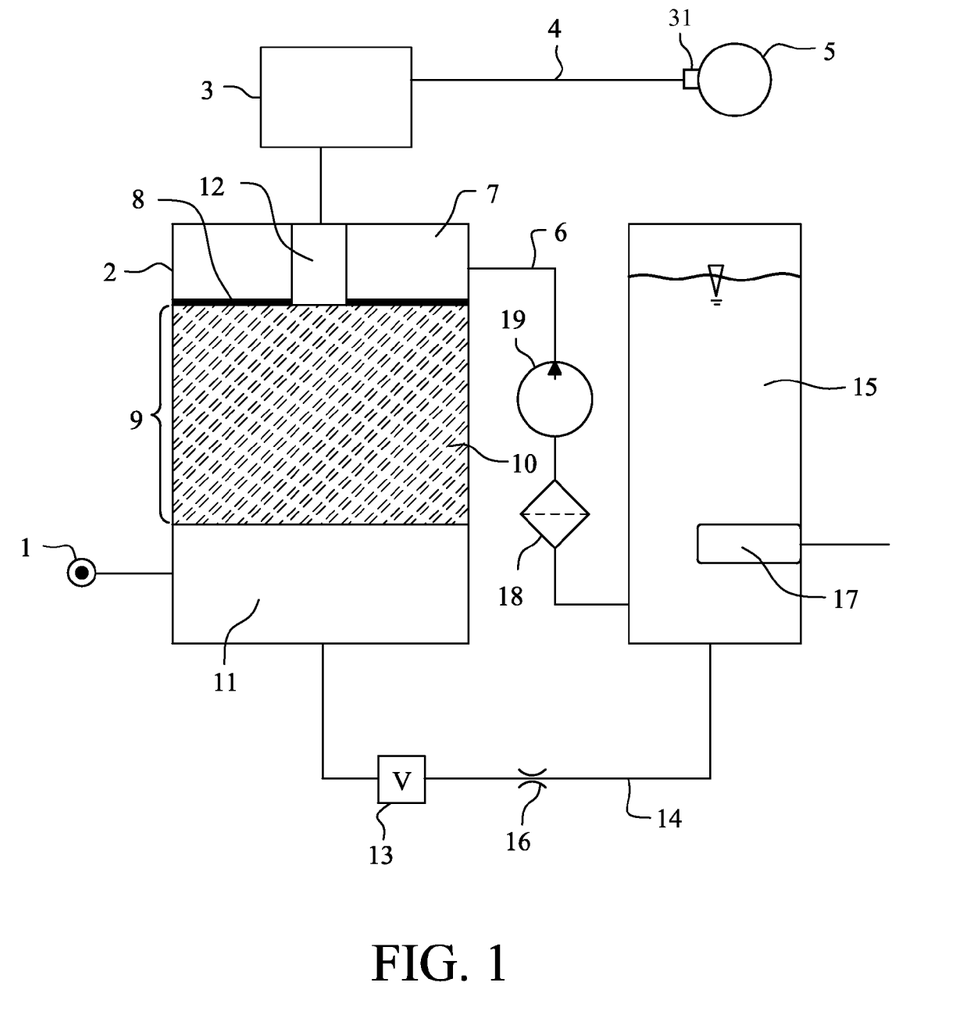
FIG. 1 is a schematic view of a device to heat and humidity gas for humidification of pressurized gas for application with a ventilator.

FIG. 1 gives the exemplary design of a humidifier according to the here presented invention. In this design the gas first enters the humidifier, then the respiratory gas flow generator.

The embodiment shows how the respiratory gas is taken from a reservoir 1 (i.e. pressurized gas or wall outlet). While passing the humidifier 2 the usually very dry pressurized gas is conducted to a respiratory gas flow generator 3. Within the respiratory gas flow generator 3 the gas is depressurized to the respiratory pressure level needed for ventilation or respiratory therapy which might be slightly above ambient air pressure. Then the respiratory gas is conducted to the patient 5 via a patient interface device 31, using active temperature controlled respiratory tubing 4 connected to the respiratory gas generator.

In this embodiment the compressible volume of the breathing system leading from the respiratory gas flow generator 3 to patient 5 is very low.

It is important that the respiratory gas conducted to the patient is of both constant and preset humidity and temperature. The preset humidity at 37° C. typically is near saturation (i.e. 100%). It is also important that the patient can be ventilated without interruption.

This is ensured by conducting heated fluid (in the given exemplary design water of 72° C.) via line 6 to the humidifier 2 and from there into the annulus 7. Here water means any fluid which might be chosen by a man skilled in the art according to requirements. In this embodiment there might be added drugs or other substances to the fluid without special notice in the following paragraphs.

The heated gas leaves the annulus 7 via a sieve bottom 8 into a sprinkling type chamber 9 filled with filling material 10. In this exemplary design this filling is made of solid structured elements inheriting a huge surface and large cut-outs.

While water is trickling from the annulus 7 via the huge surface downwards into the bottom chamber 11 of the humidifier 2 it heats and wets the filling material 10. At the same time respiratory gas from reservoir 1 is flowing in the opposite direction through the filling 10. By doing so the respiratory gas is heated and humidified. In the end the nearly saturated gas is conducted via the collecting chamber 12 to the respiratory gas flow generator 3.

Here it should be pointed out that the flow of heated water is substantially higher than the water flow needed to humidify the respiratory gas to saturation. This is to guarantee that there is no significant cooling of the fluid in the contact area of gas and fluid, and that the gas flow is heated as required.

With the here illustrated design the above mentioned process is working under pressure. Water and respiratory gas are pressurized to 4.5 bar. The temperature is about 72° C.

Depressurization of the respiratory gas from 4.5 bar/72° C. to nearly environmental pressure/37° C. ensures that the depressurized respiratory gas has a relative humidity of nearly 100%.

The humidifier will also work with other temperature/pressure combinations as long as it is guaranteed that even after depressurization to the respiratory pressure level at the target temperature the respiratory gas will be humidified according to the target humidity.

As explained above humidifier 2 collects the fluid which has trickled through the filling material in the bottom chamber 11. Controlled by valve 13 it is conducted via a backflow line 14 into a reservoir 15, passing a depressurizer 16. Thus the reservoir 15 is depressurized. The here discussed design inherits a choke-like depressurizer.

In the embodiment, the water temperature inside the reservoir 15 is heated by a controlled heater to 72° C. which is technically quite easy to construct. The heated water is forced by a pump via an optional filter 18 through line 6 back to the annulus 7 of the humidifier 2.

The optional filter 18 guarantees that the recirculated water, and in consequence the respiratory gas flowing into the respiratory gas flow generator 3 is nearly free of particles or microorganisms.

Since there are present pump 19, valve 13 and/or depressurizer 16, the reservoir 15 can be of the low-pressure type and may be refilled at any time.

Figure 2:
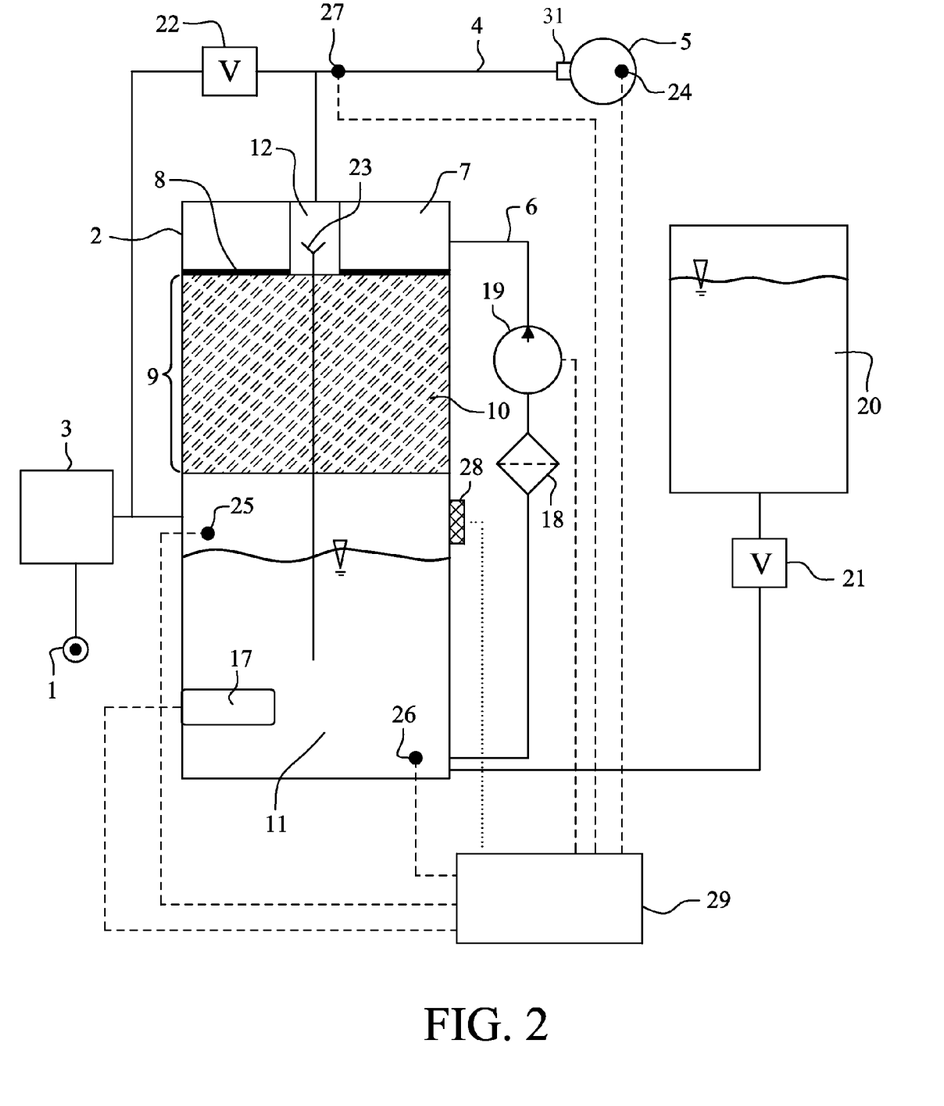
FIG. 2 shows a schematic view of another embodiment of a device for heating and humidification of gas lacking a pressurized circuit area.

FIG. 2 shows an alternative embodiment where the humidifier 2 is placed between the respiratory gas flow generator 3 and the patient 5 as it is in conventional state-of-the-art designs (see above).

In order to keep small both the compressible volume and physical dimensions of the device, the device is designed to handle the range of gas flows used in respiratory therapy (0 to 180 l/min), and its humidification power is complying with the respective standards.

Warmed fluid (in this example heated to about 37° C. is conducted via line 6 to the humidifier 2 where it enters the distribution chamber 7.

From the distribution chamber 7 the heated water circulates through the sieve bottom 8 into a sprinkling type chamber 9 filled with filling material. In this example the filling is made from solid structured elements with a huge surface and large cut-outs.

In order to simplify the design one could do without the filling 10 and make the fluid coming from the sieve bottom 8 simply drop through the sprinkling type chamber 9. Under certain conditions this might be regarded advantageous for purposes of cleansing and reprocessing of the humidification chamber. It might well be, however, that in order to get the same performance with respect to humidification both the volume of the sprinkling type chamber and the circulated fluid volume flow have to be substantially increased.

The water coming from the distribution chamber 7 trickling along the huge surface downwards into the bottom chamber 11 of the humidifier 2 is heating and wetting the filling 10. Simultaneously by streaming counterwise through the filling 10 the respiratory gas coming from the respiratory gas flow generator 3 is heated and humidified. Nearly saturated (relative humidity 95 to 100%) it streams via the collecting chamber to the patient 5.

In order to avoid condensate formation preferably a temperature-controlled actively heated respiratory tubing 4 of known conventional technology is used. For the same reason it is of importance that the temperature of any part of the tubing's wall in contact with the gas is equal or above the gas saturation temperature. Usually the gas in the respiratory tubing 4 is heated to a temperature slightly higher, i.e. 40° C., in order to prevent condensate formation even at the last few centimeters of the patient sided respiratory tubing and especially the unheated endotracheal tube.

One should also mention that dependent on the working principle of the particular respiratory gas flow generator 3 model used only a single, or multiple respiratory tubings 4, may be used. The patient's expiratory gas might even be recirculated to the respiratory gas flow generator. Under those circumstances the discussion above with respect to necessity and possibilities of heated respiratory tubing references also to all other types of respiratory tubing and parts thereof where there is the risk of condensate formation.

As already discussed, humidifier 2 collects the fluid trickling through filling 10 into its bottom chamber 11 which functionally is a fluid reservoir.

Here by means of the temperature-controlled heater 17 the fluid is heated to a constant temperature of in the embodiment 37° C. The design of such a temperature-controlled heater is technically simple. The heated water is forced by pump 19 through the optional filter 18 and line 6 back to the distribution chamber 7 of the heater 2.

The optional filter 18 guarantees that both the circulated water, and in consequence the respiratory gas conducted to the patient 5, are nearly free of particles or microorganisms. Alternatively or as a supplement the device may inherit an antibacterial inner surface.

The fluid level in the bottom chamber 11 may be regulated to a constant level by means of valve 21 controlling the fluid flow from a fluid reservoir 20 (i.e. a bottle as commonly used for iv infusion). Valve 21 may well be constructed as flotation type valve. In this case it is important that the hydrostatic pressure difference between fluid reservoir 20 and bottom chamber 11 is always higher than the highest possible peak respiratory gas pressure. In practice the fluid reservoir 20 should be positioned at least 1 m above the bottom chamber 11.

For reasons of patient safety another valve 22 controls a bypass between the humidifier's 2 gas inlet and gas outlet in order to ensure that with a high difference pressure (i.e. provoked by a humidifier failure) respiration is left unimpaired.

Surplus water and water trapped by the air is separated in the water trap 23 integrated into the collection area 12. This water is recirculated into the bottom chamber 11.

For purposes of control of the humidification process and monitoring of the device's proper function the control-and-monitoring device 29 is connected to the humidifier 2 and the patient 5 by means of several sensors and control lines. The temperature sensor 24 which may be of one of those sensor types commercially easily available is sensing the patient's temperature which may be fed into the humidification process as target temperature. Alternatively the target temperature may be dictated by another device, i.e. a patient monitoring device, communicating with the control-and-monitoring device 29. The fluid temperature is measured by another temperature sensor 26 and controlled with heater 17.

The third temperature sensor 25 is sensing the gas temperature at the gas inlet. In case of a too high fluid level in the bottom chamber 11 due to a failure of valve 21 or pump 19 the control-and-monitoring device 29 is able to detect an unduly high fluid level by means of detecting the increase in temperature at the site of temperature sensor 25. In such a case the bypass valve 22 will open. In consequence the temperature sensor 27 sensing the gas temperature at the gas outlet will detect a markable decrease in temperature. This security mechanism may be checked by voluntarily switching off the pump 19; in consequence, the fluid level should increase if the mechanism is working properly.

The humidifier 2 is connected with the control-and-monitoring device 29 via the transponder 28 firmly connected to the humidifier 2, in order to identify the humidifier and to monitor with regard to its lifetime.

The control-and-monitoring device 29 is also able to monitor the power consumption of pump 19. Since the pump's power consumption is a function of the fluid level in the bottom chamber 11, the control-and-monitoring device 29 is also able to detect a too low fluid level (i.e. due to an empty fluid reservoir 20, failure of valve 21, or failure of the fluid circulation due to an obstructed sieve bottom 8).

Figure 3:
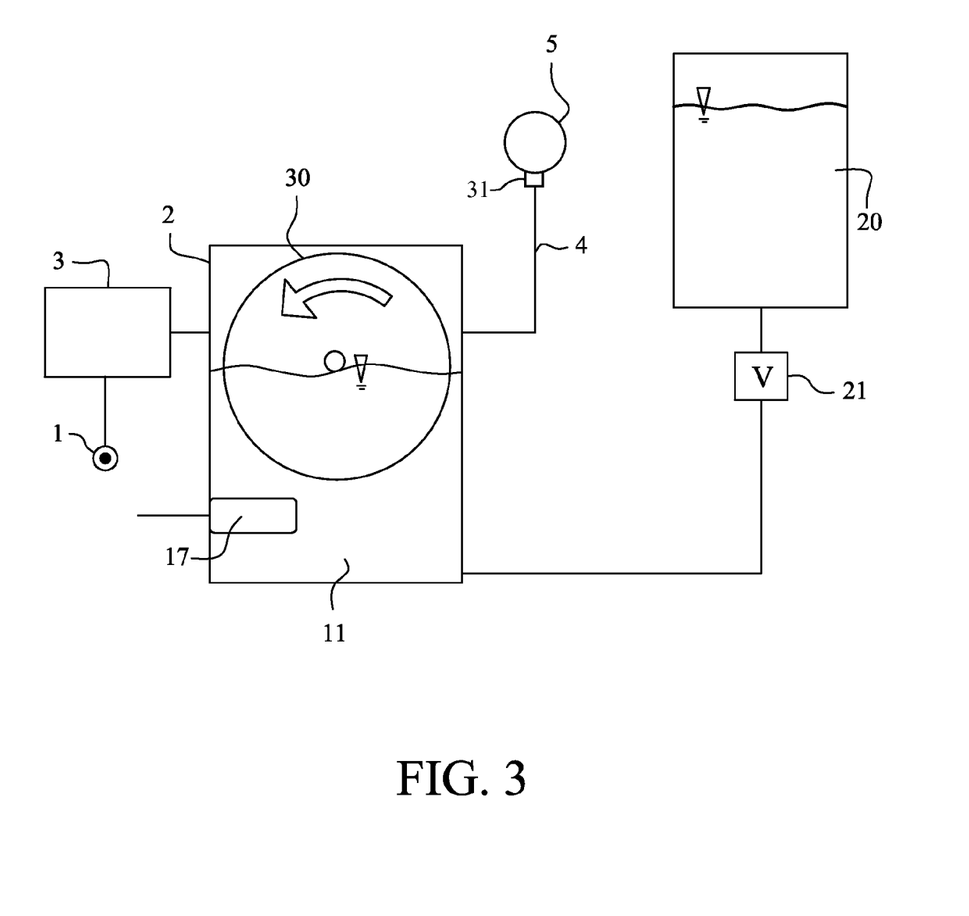
FIG. 3 shows still another schematic view of an alternative embodiment comprising a drive device using a stack of plates.

An alternative design might be as shown in FIG. 3.

The humidifier 2 according to FIG. 2 is placed in this embodiment between the respiratory gas flow generator 3 and patient 5. The fluid is in a bottom chamber 11, and its temperature is controlled to a preset value by means of the heater 17.

The fluid in the bottom chamber 11 is held at a constant level by means of the fluid reservoir 20 and valve 21 as within FIG. 2.

Solid structured elements of the exchanger device 30 are periodically (preferably by means of rotation) partially submerged into the fluid in order to achieve a sufficient frequent exchange of the water within the contact area. During this procedure the geometrical design or the structured elements (i.e. radial ribs, or similar) has a significant impact on the amount of fluid taken along during the phase of submerging. A high rotation frequency may further increase the energy transport.

If designed according to FIGS. 1 to 3 and correctly dimensioned a heavily varying or intermittently interrupted gas flow can be conditioned to nearly constant temperature and humidity. There is no risk of overheated gas after sudden gas flow interruption and there is no risk of a too low humidity if the gas flow suddenly becomes very high.

In order to perform the object of the here presented invention the fluid/gas interface has to be dimensioned and equipped with such a geometric structure that even in case of the maximally allowed peak gas flow the energy and mass transfer can take place completely. The proper dimensioning may be checked by conducting the maximum allowed peak gas flow through the device according to the present invention. If dimensioned correctly the gas temperature after having passed the humidification chamber is nearly identical to that of the fluid before it enters the humidification chamber.

Suitable measures (i.e. increasing the effective flow cross-sectional area) will prevent the dragging of water droplets along by the gas.

The use of heated respiratory tubing for the further transport of the gas will effectively prevent condensate formation within the tubing.

In case there is the need to humidify the gas to less than saturation this may be realized by switching a suitable heater element into the stream of the already humidified gas. The humidifier according to the here presented invention conditions the gas to a temperature and humidity where the absolute humidity is according to requirements. The additional gas heater at the gas outlet, and/or the addition of dry gas, will adjust both the temperature and relative humidity of the gas to the target values. Thus it is possible to generate gas of various combinations of temperature and humidity.

The device according to the here presented invention is suitable not only for purposes of respiratory therapy but for all applications where a variable gas flow has to be cleansed of particles and/or conditioned to a preset/constant temperature or humidity. Application examples are the insufflation of gases into body cavities (i.e. carbon dioxide: laparoscopy), the provision of respiratory gas in breathing protection applications (i.e. painting), all types of inhalation, and air conditioning (i.e. of houses, vehicles, airplanes) alone or in combination with other air-conditioning devices.

What is claimed is:

1. A humidifier system to heat and humidify a supply of gas with a fluid, the humidifier system comprising:
    a humidifier device having a gas inlet, a gas outlet, and at least one wall defining a humidification chamber structured to contain the fluid;
    a humidification surface to heat and humidify the supply of gas, the humidification surface positioned in the humidification chamber and between the gas inlet and the gas outlet such that in use the supply of gas flows from the gas inlet, passes through the humidification surface, and exits from the gas outlet;
    a controlled heater device positioned to heat the fluid contained in the humidification chamber;
    a control-and-monitoring device configured to control and monitor the humidifier device and configured to control the controlled heater device;
    a drive device configured to move the fluid through the humidification surface and the gas; and
    a transponder firmly connected to the at least one wall of the humidifier device and configured to communicate wirelessly with the control-and-monitoring device to identify the humidifier device,
    wherein the control-and-monitoring device is configured to monitor a power consumption of the drive device to detect that a fluid level of the humidifier device is too low based on the power consumption of the drive device.

2. A humidifier system according to claim 1, wherein the fluid and the gas are moved through the humidification surface in opposite directions.

3. A humidifier system according to claim 1, further comprising a filling material in said humidifier device, the humidification surface comprising the filling material.

4. A humidifier system according to claim 3, wherein the filling material includes knitted aluminium, stainless steel wool, or metal pearls.

5. A humidifier system according to claim 3, wherein the filling material is removable.

6. A humidifier system according to claim 1, wherein said humidifier device is pressurized.

7. A humidifier system according to claim 1, further comprising:

a fluid reservoir structured to hold a supply of the fluid; and a fluid line connected to the fluid reservoir to deliver the fluid from the fluid reservoir to the humidifier device.

8. A humidifier system according to claim 7, wherein said drive device is a pump feeding the fluid from the fluid reservoir to the humidification surface, the humidification surface and the fluid reservoir being connected in a circuit.

9. A humidifier system according to claim 7, wherein the humidifier device comprises a bottom chamber to collect the fluid that has passed through the humidification surface.

10. A humidifier system according to claim 9, wherein the fluid collected in the bottom chamber is recirculated back to the fluid reservoir.

11. A humidifier system according to claim 1, wherein the humidification surface includes a sieve surface configured to distribute the fluid within the humidifier device.

12. A humidifier system according to claim 1, wherein the humidification surface is configured to provide a large surface area for humidity exchange.

13. A respiratory system to provide a supply of pressurized humidified gas to a patient, the respiratory system comprising:

a humidifier system according to claim 1 to humidify the supply of gas;

a gas flow generator coupled to the humidifier device configured to control the pressure of the supply of gas; and a patient interface device coupled to an air delivery tube structured to deliver the pressurized, humidified supply of gas to the patient.

14. A respiratory system according to claim 13, wherein the gas flow generator is provided downstream of the humidifier device.

15. A respiratory system according to claim 14, wherein the supply of gas for the humidifier device is provided from a gas reservoir.

16. A respiratory system according to claim 13, wherein the gas flow generator is provided upstream of the humidifier device.

17. A respiratory system according to claim 13, further comprising at least one sensor to measure at least one of patient temperature, inlet gas temperature, outlet gas temperature, and fluid temperature.

18. A respiratory system according to claim 17, wherein each at least one sensor is configured to communicate with the control-and-monitoring device.

19. A respiratory system according to claim 13, further comprising a bypass valve configured to allow the supply of gas to bypass the humidifier device to ensure pressurized gas is provided to the patient if the humidifier system fails.

20. A humidifier system according to claim 1, wherein the control-and-monitoring device is further configured to detect a fluid level of the humidifier device.

* * * * *